United States Patent [19]

Hata et al.

[11] 4,428,951
[45] Jan. 31, 1984

[54] LONG ACTING PHARMACEUTICAL COMPOSITION

[75] Inventors: Takehisa Hata, Muko; Kenichi Nishimura, Takatsuki; Mitsuru Yasumura, Nishinomiya, all of Japan

[73] Assignee: Fujisawa Pharmaceutical Co., Ltd., Osaka, Japan

[21] Appl. No.: 370,668

[22] Filed: Apr. 22, 1982

[51] Int. Cl.³ .................. A61K 9/22; A61K 9/52; A61K 31/495
[52] U.S. Cl. .................................. 424/250; 424/19
[58] Field of Search ..................... 424/250, 19

[56] References Cited

U.S. PATENT DOCUMENTS 4,017,614 4/1977 Wild ............................. 424/232
4,102,806 7/1978 Kondo et al. ................. 424/38
4,175,085 11/1979 Binder et al. ................. 424/275

OTHER PUBLICATIONS

Merck Index, 9th Ed., (1976), p. 1216.

Primary Examiner—Stanley J. Friedman
Attorney, Agent, or Firm—Oblon, Fisher, Spivak, McClelland & Maier

[57] ABSTRACT

The present invention relates to a long active pharmaceutical composition of Tiaramide or its pharmaceutically acceptable salt which comprises Tiaramide or its pharmaceutically acceptable salt as an active ingredient and a water particularly insoluble substance which melts with warming or heating.

4 Claims, No Drawings

LONG ACTING PHARMACEUTICAL COMPOSITION

BACKGROUND OF THE INVENTION

1. Field of the Invention

This invention relates to a long acting pharmaceutical composition of Tiaramide or its pharmaceutically acceptable salt.

More particularly, this invention relates to a long acting pharmaceutical composition which comprises Tiaramide or its pharmaceutically acceptable salt as an active ingredient and a water-particularly insoluble solid substance which melts with warming or heating.

2. Description of the Prior Art

Tiaramide, i.e. 3-[4-(2-hydroxyethyl-1-piperazinyl)-carbonylmethyl]-5-chloro-2-benzothiazolinone or its pharmaceutically acceptable salt as used as an active ingredient in this invention is widely known as an excellent analgesic, antiallergic and antiinflammatory medicine, among which, Tiaramide hydrochloride is marketted in a form of tablet for oral administration use.

As to Tiaramide or its pharmaceutically acceptable salt, it is understood that said drug is very rapidly absorbed in the body, for example, its serum concentration in human beings comes up to the maximum within about one hour after its oral administration.

However, Tiaramide or its pharmaceutically acceptable salt is excreted so rapidly that more than 90% of Tiaramide is excreted in the urine within about 20 hours after its administration, and accordingly its serum concentration decreases rapidly in a short time after its administration.

Due to the behavior of Tiaramide or its pharmaceutically acceptable salt as explained above, it is necessary for patients to take the drug many times a day for efficient therapy.

SUMMARY OF THE INVENTION

After extensive studies of various pharmaceutical compositions, the problem as given above has been solved based upon the new finding that the inventors of this invention have found out a long acting pharmaceutical composition of Tiaramide or its pharmaceutically acceptable salt which comprises Tiaramide or its pharmaceutically acceptable salt as an active ingredient and a water-particularly insoluble solid substance which melts with warming or heating (hereinafter referred to as "water-particularly insoluble solid substance") for efficient therapy.

Namely, according to this invention, efficient therapy can be achieved by the less dosage and less administration times of Tiaramide or its pharmaceutically acceptable salt, since the serum concentration of Tiaramide or its pharmaceutically acceptable salt can be maintained for a long time by administration of the composition of this invention to human beings.

Suitable pharmaceutically acceptable salt of Tiaramide to be used in this invention may include hydrochloride and any other pharmaceutically acceptable acid addition salt.

Suitable "water particularly insoluble solid substance which melts with warming or heating" may include paraffin, carnauba wax, hydrogenated oil and the like.

The long acting pharmaceutical composition of this invention can be used in a conventional pharmaceutical form such as tablet.

Preferable amount of "water-particularly insoluble solid substance which melts with warming or heating" to "whole amount of the composition" is 2 to 40 weight percent (more preferably 3 to 30 weight percent and the most preferably 5 to 20 weight percent).

Preferable amount of Tiaramide or its pharmaceutically acceptable salt can be suitably selected. For example, in case that Tiaramide hydrochloride is used as an active ingredient in this invention, preferable amount of "Tiaramide hydrochloride" to "whole amount of the composition" is 40 to 90 weight percent (more preferably 50 to 85 weight percent).

Furthermore, the long acting pharmaceutical composition of this invention can be prepared without any particular solvent, since the "water-particularly insoluble solid substance" used in this invention can also serve as a solvent in a liquid form under warming or heating. Therefore, according to this invention, it is unnecessary to remove any solvent for preparing the long acting pharmaceutical composition of this invention. For example, in case that the long acting pharmaceutical composition of this invention is tablet, it can be prepared by mixing Tiaramide or its pharmaceutically acceptable salt with the melted "water-particularly insoluble solid substance" under warming or heating, and by granulating the resulting mixture and then by compressing it into tablet.

The pharmaceutical composition of this invention may contain various organic or inorganic additives, which are conventionally used for the purpose of pharmaceutical preparation, such as excipient (e.g. lactose, starch, sucrose, etc.), binding agent (e.g. starch, hydroxypropyl cellulose, polyvinylpyrrolidone, gelatin, etc.), disintegrator (e.g. microcrystalline cellulose, starch, carboxymethyl cellulose, etc.), lubricant (e.g. talc, magnesium stearate, etc.), or the like.

The following comparative test data are given to illustrate superiority of the pharmaceutical composition of this invention in comparison with the commercially available Tiaramide hydrochloride tablet.

EXPERIMENT

(1) DISSOLUTION TEST

The dissolution rate of each tablet obtained in Examples of this invention and the commercially available tablet (110 mg of Tiaramide hydrochloride is contained) was determined according to the rotating basket method (J.P.X Method I.) under 100 r.p.m. were simulated gastric juice (J.P.X Disintegration Test Solution No. 1).

The results are shown in the following Table 1.

TABLE 1

| Tablet | Dissolution rate (%) Time (hour) | | | | | | |
|---|---|---|---|---|---|---|---|
| | ¼ | 0.5 | 1 | 2 | 4 | 5 | 6 |
| Commercially available tablet | 92 | 100 | — | — | — | — | — |
| Example 1 | — | — | 33 | 45 | 61 | 66 | 71 |
| Example 2 | — | — | 35 | 48 | 64 | 70 | 75 |
| Example 3 | — | — | 30 | 41 | 56 | 60 | 64 |
| Example 4 | — | — | 31 | 44 | 60 | 66 | 71 |

(2) BIOAVAILABILITY TEST IN DOGS

The one tablet weighing 320 mg (220.4 mg of Tiaramide hydrochloride is contained) obtained in Example 1 of this invention and the two commercially available tablets (total amount of Tiaramide hydrochloride is 220.4 mg) were orally dosed to 12 beagle dogs, respectively, and then the serum concentration of Tiaramide was determined by gas-liquid chromatography.

The results were shown in the following Table 2.

TABLE 2

| Tablet | Mean serum concentration (μg/ml) of Tiaramide Time (hour) | | | | | | | | |
|---|---|---|---|---|---|---|---|---|---|
| | 0.5 | 1 | 2 | 4 | 6 | 8 | 10 | 12 | 24 |
| Commercially available tablet | 1.5 | 4.8 | 2.7 | 0.4 | 0.4 | 0.3 | — | — | — |
| Tablet (320 mg) of Example 1 | — | 1.7 | 2.3 | 1.9 | 1.6 | 1.1 | 0.8 | 0.6 | 0.2 |

According to the above experimental results, it can be said that the long acting pharmaceutical composition of this invention is much superior to the marketting tablet for efficient therapy of patients.

The following Examples are given to illustrate this invention, but this invention is not limited thereto.

DESCRIPTION OF THE PREFERRED EMBODIMENTS

EXAMPLE 1

Tiaramide hydrochloride (70 weight parts) was reduced to powder and warmed at about 70° C., to which melted paraffin (6 weight parts) at 80° to 90° C. was added, and the mixture was granulated. To the resulting granule was added melted macrogol 6000 (polyethylene glycol) (18 weight parts) at 80° to 90° C., and the mixture was granulated in 1000 to 50μ size. The resulting granule was blended with a mixture of magnesium stearate (5 weight part) and light anhydrous silicic acid (1 weight part) and then compressed into tablet weighing 313 mg. Thus obtained tablet was coated with coating liquid or hydroxypropyl methylcellulose until the weight of the coating solid part of the tablet became 7 mg.

EXAMPLE 2

Melted hydrogenated oil (11 weight parts) at 80° C. was blended with powdered Tiaramide hydrochloride (85 weight parts) and then granulated in 1000 to 50μ size. Thus obtained granule was blended with magnesium stearate (4 weight parts) and then compressed into tablet weighing 259 mg.

EXAMPLE 3

Melted carbon wax (19 weight parts) at 90° C. was blended with a mixture of Tiaramide hydrochloride (52 weight parts) and lactose (27 weight parts) and then granulated in 1000 to 50μ size. Thus obtained granule was blended with magnesium stearate (2 weight parts) and then compressed into tablet weighing 420 mg.

EXAMPLE 4

Melted paraffin (19 weight parts) at 80° to 90° C. was blended with Tiaramide hydrochloride (77 weight parts) and then granulated in 1000 to 50μ size. Thus obtained granule was blended with magnesium stearate (4 weight parts) and then compressed into tablet weighing 285 mg.

What we claim is:

1. A long-acting pharmaceutical composition in tablet form for the oral administration of Tiaramide, which comprises: a pharmaceutically effective amount of Tiaramide or pharmaceutically acceptable salt thereof as an active ingredient dissolved in a water-insoluble solid vehicle selected from the group consisting of carnabua wax, hydrogenated oil and a paraffin.

2. The composition of claim 1, wherein the amount of said Tiaramide or pharmaceutically acceptable salt thereof present in said composition ranges from 40 to 90 wt. %.

3. The composition of claim 1, wherein said water-insoluble solid vehicle is present in said composition in an amount of 2 to 40% by weight.

4. The composition of claim 1, wherein said composition further comprises an excipient, a binding agent, a disintegrator, a lubricant or various combinations of these ingredients.

* * * * *